Figure 1:
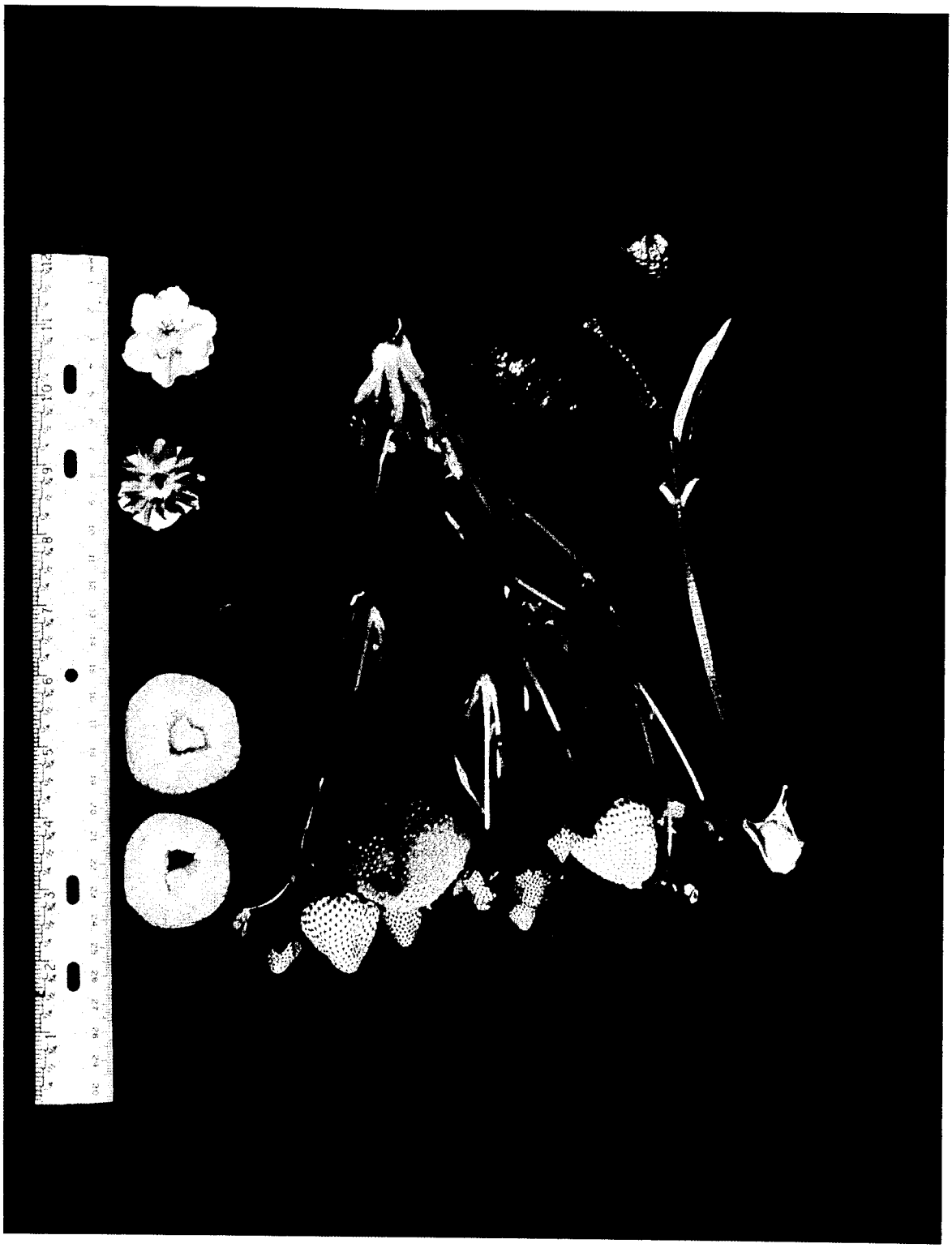

United States Patent [19]

Johnson, Jr.

[11] Plant 4,387

[45] Feb. 27, 1979

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 886,703

[22] Filed: Mar. 15, 1978

[51] Int. Cl.[2] ..... A01H 5/03

[52] U.S. Cl. ..... Plt./48

[58] Field of Search ..... Plt./48–49

*Primary Examiner*—Robert E. Bagwill

[57] ABSTRACT

A variety of strawberry characterized by its adaptation to Southern California culture, its good vigor, and abundant runners.

1 Drawing Figure

1

This invention relates to a new and distinct variety of strawberry plant known as H5 which is the result of a cross of the unpatented varieties known as the Driscoll Strawberry Associates' selections G7 and G8.

Seedlings resulting from the aforementioned cross were grown and asexually multiplied in Shasta County, Calif., and tested in the fruiting beds on the property of member growers of Driscoll Strawberry Associates, Inc. Clones of the seedlings were also held at the Propagation Nursery in Shasta County. One plant was selected from the aforementioned group of seedlings and further asexually reproduced in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising commercial variety.

FIG. 1 of the accompanying drawing illustrates plant parts of the new variety, typical in size, shape and color.

A berry in cross section illustrates flesh color and characteristic core cavity of a berry that would be mature enough to be picked, but not totally ripe. The inflorescence pictured illustrates typical branching and relative size during April in Oxnard. The pedicel holding the primary berry early in the spring originates from the axil and this axil originates near the crown with very little of any primary peduncle present, as is illustrated. As the fruiting season progresses half or more of the pedicels holding the primary berry originate from one of the peduncles that form the axil. Also, as the season progresses the total length of the inflorescence becomes larger than that illustrated.

The near ripe berry is typical of primary fruit, large globose to short conic to short wedged in outline as is illustrated in the U.S.D.A. Bulletin 1043. As is illustrated, spring primaries often produce longitudinal furrows with an acute apex which is often lighter colored than the remainder of the fruit. The surface in general, however, is smooth, producing seed that is slightly exerted. The calyx and petals shown are typical of secondary flowers and are considered medium to large in size. The leaf shown is typical, illustrating the leaflet color and texture and the petiole, petiolule and leaflet serrations during early spring.

This novel summer planted, spring variety is adapted mainly to use in Southern California. The new variety will also produce well when winter planted and mulched with polyethylene film, a common practice in Southern California. If this variety is summer planted during the first week in August in Ventura County, it

2 will produce during mid-March, but peaks during mid-April. Even though it peaks about the same time as Driscoll H4, U.S. Plant Pat. No. 3,987, the new variety produces more of its crop during late March and early April than does H4. The plant of the new variety is larger, more vigorous with larger leaflets, but lighter in color than H4. Individual leaves have longer and thicker petioles than H4, and leaflets become more rugose. The H4, however, has a thicker leaflet. Individual marginal serrations are larger on the new variety. Bracts on the petioles are less rare on the new variety than H4. The average inflorescence length of the new variety is longer than H4, especially after the first spring crop. The fruit size is larger, the color is lighter but glossier, and the seed less exerted than H4. The pedicel holding primary fruit of H4 originates at the axil of peduncles more consistently than the new variety. More berries per inflorescence are produced in the new variety. The new variety is usually more globose in outline and wider than long in contrast to H4, but the new variety will more often have a pointed apex. Frequently, there is a small concave area near the apex associated with the longitudinal furrow that is present on the primaries which is unique and different than that of H4. Except for the early spring crop the flowers of the H4 are more visible above the plant. The aroma of the new variety is not distinctive, but is more noticeable than the H4 when the fruit is confined to a small space such as inside a polyethylene bag. This variety has had only limited exposure to the two-spotted mite, mildew and the Mycosphaerella leaf spot, but appears to be equally susceptible to these pests as H4. The new variety is a prolific runner producer both at the nursery and in the fruiting bed as is H4, but the runner plants from the nursery are larger.

As a seedling and selection this new variety withstood the natural invasions of certain virus components found in Central and Southern California without losing its ability to produce.

The varietal characteristics of the novel plant, described below in detail, were observed mainly during the spring and June in Oxnard, but observations were also made in the late summer in Watsonville, which is a cool coastal area near the Pacific Ocean. The drawing was taken in Oxnard on April 1.

The color terminology as used herein is in accordance with Ridgway's Color standards and Nomenclature (1912 Edition).

Plant: Large, vigorous and establishes multiple crowns readily when planted during August. It has an extensive root system.

Leaves: Large in size, central leaflet is mostly 7 to 9 cm. length with the width less than the length. Petiole length is long during late fruiting season, averaging 21 cm. in length during June, but considerably shorter in April. Petiolule medium to long, averaging 11 to 12 mm. Bracts on the petioles are rare. The leaflet surface is mildly rugose and there is an irregular cupping upward of some leaves but most leaflets are held in an irregular position. Serrations at the margins of leaflets are large with many becoming noticeably deep, ovate and short acute in outline. Color of leaflet is Ivy Green, Plate XXXI.

Runners: Runners are vigorous and abundant, both at the nursery and the fruiting bed.

Inflorescence: Medium to long in length, becoming longer as the season progresses 25 to 30 cm. in June. Common peduncle very short during March production, becoming medium in length during June, mostly 12 to 16 cm. Pedicel holding the primary berry originates from the axil of peduncles about half the time and half the time it originates at various locations on the peduncle. Flowers are medium to large, producing an abundance of pollen even in early spring. Flowers visible above the plant during early spring, not as obvious in late spring and summer. Hair on pedicels holding tertiary berries 20 cm. from the berry, irregularly parallel to the pedicel.

Fruit: The first fruit produced during the spring after a summer planting is large. Subsequent crops produce smaller size with tertiaries considerably smaller than primaries. Primary berries during June are 35 to 45 mm. in length with the width mostly greater than the length. Fruit shape is mostly globose conic to globose wedge. Primary fruit that is globose conic often has a small longitudinal furrow that reaches the apex, leaving a small depressed area near the apex (see drawing). The apex is often lighter in color than the rest of fruit surface, even though the seed is fertilized. The shoulders near the calyx are rounded not necked. Seed is generally yellow, but darkens when exposed to direct sunlight. The seed is generally held equal to the surface or is slightly exerted. The fruit is considered firm, especially during the spring crop. The core is medium in size. The flesh is medium in firmness and rates good in flavor panels. The color of the fruit surface is Scarlet Red, Plate I and the flesh Scarlet to White, Plate I.

Calyx: Medium to large in diameter in relation to fruit size 35 to 45 mm. Sepals mostly 13 to 15 in number. Serrations may be present on primary berries and the sepals generally overlap each other. Color of sepals on the side facing the fruit is Cress Green, Plate XXXI.

I claim:

1. The new and distinct variety of strawberry plant herein described and illustrated, and identified by the characteristics enumerated above.

* * * * *